(12) United States Patent
Lambert

(10) Patent No.: US 6,275,650 B1
(45) Date of Patent: Aug. 14, 2001

(54) GAS SUPPLY APPARATUS AND METHOD FOR THE SUPPLY OF TREATMENT GAS TO A PERSON OR TO AN ANIMAL

(75) Inventor: Hans Lambert, Stockholm (SE)

(73) Assignee: Hudson Respiratory Care Inc., Temecula, CA (US)

( * ) Notice: Subject to any disclaimer, the term of this patent is extended or adjusted under 35 U.S.C. 154(b) by 0 days.

(21) Appl. No.: 09/402,443
(22) PCT Filed: Apr. 6, 1998
(86) PCT No.: PCT/SE98/00633
   § 371 Date: Oct. 6, 1999
   § 102(e) Date: Oct. 6, 1999
(87) PCT Pub. No.: WO98/44977
   PCT Pub. Date: Oct. 15, 1998

(30) Foreign Application Priority Data

Apr. 7, 1997 (SE) ................................... 9701262

(51) Int. Cl.$^7$ .............................. F24F 6/08; A61M 15/00
(52) U.S. Cl. ........................................ 392/395; 128/203.12
(58) Field of Search ................................. 392/386, 387, 392/394, 395, 400, 401, 402, 403, 404, 405, 406; 128/203.12, 203.13, 203.15, 203.16, 203.17, 203.25, 203.26, 203.27, 204.13, 204.21, 204.22

(56) References Cited

U.S. PATENT DOCUMENTS

| | | | |
|---|---|---|---|
| 3,820,540 | * 6/1974 | Hirtz et al. | 128/203.27 |
| 4,110,419 | * 8/1978 | Miller | 218/203.27 |
| 4,484,576 | * 11/1984 | Albarda | 128/203.27 |
| 4,914,719 | * 4/1990 | Conlon | 250/339.13 |
| 4,943,704 | * 7/1990 | Rabenau et al. | 128/203.12 |
| 5,259,995 | 11/1993 | Matalis . | |
| 5,509,405 | * 4/1996 | Mashak | 128/203.12 |
| 5,536,323 | 7/1996 | Kirlin et al. . | |

FOREIGN PATENT DOCUMENTS 2 255 912   11/1992 (GB) .

* cited by examiner

Primary Examiner—Sang Paik
(74) Attorney, Agent, or Firm—Knobbe, Martens Olson & Bear, LLP

(57) ABSTRACT

A gas supply apparatus for supplying anesthetic to a human or animal. A vaporizer has a vaporization chamber which includes a gas inlet and outlet. A liquid emitting device in the vaporization chamber communicates with an external liquid source through a liquid delivery. The liquid to be vaporized is exposed to the bypassing gas by way of the liquid emitting device. The liquid is exposed exclusively by way of the porosities in the liquid emitting device. A heater is provided for heating said liquid.

21 Claims, 8 Drawing Sheets

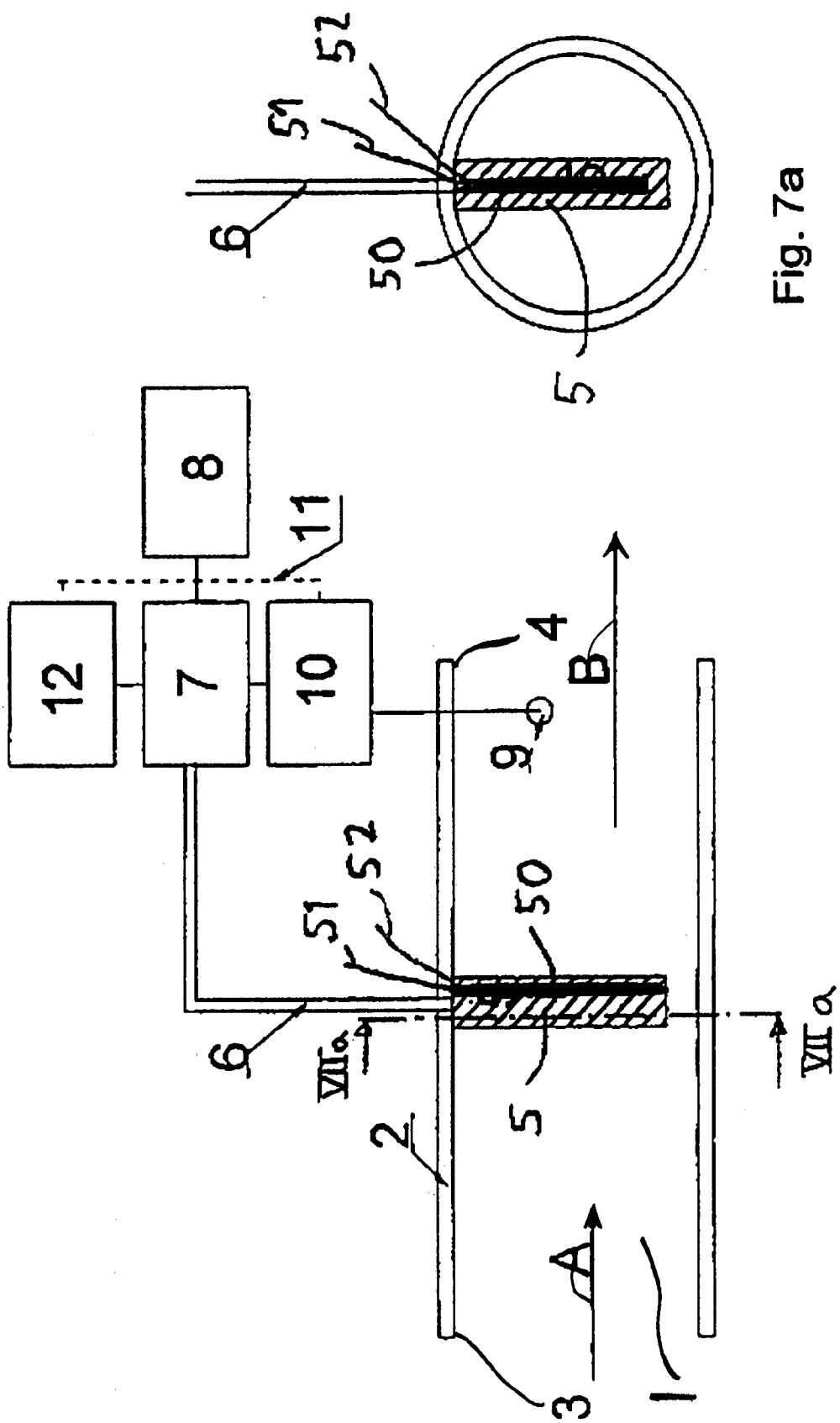

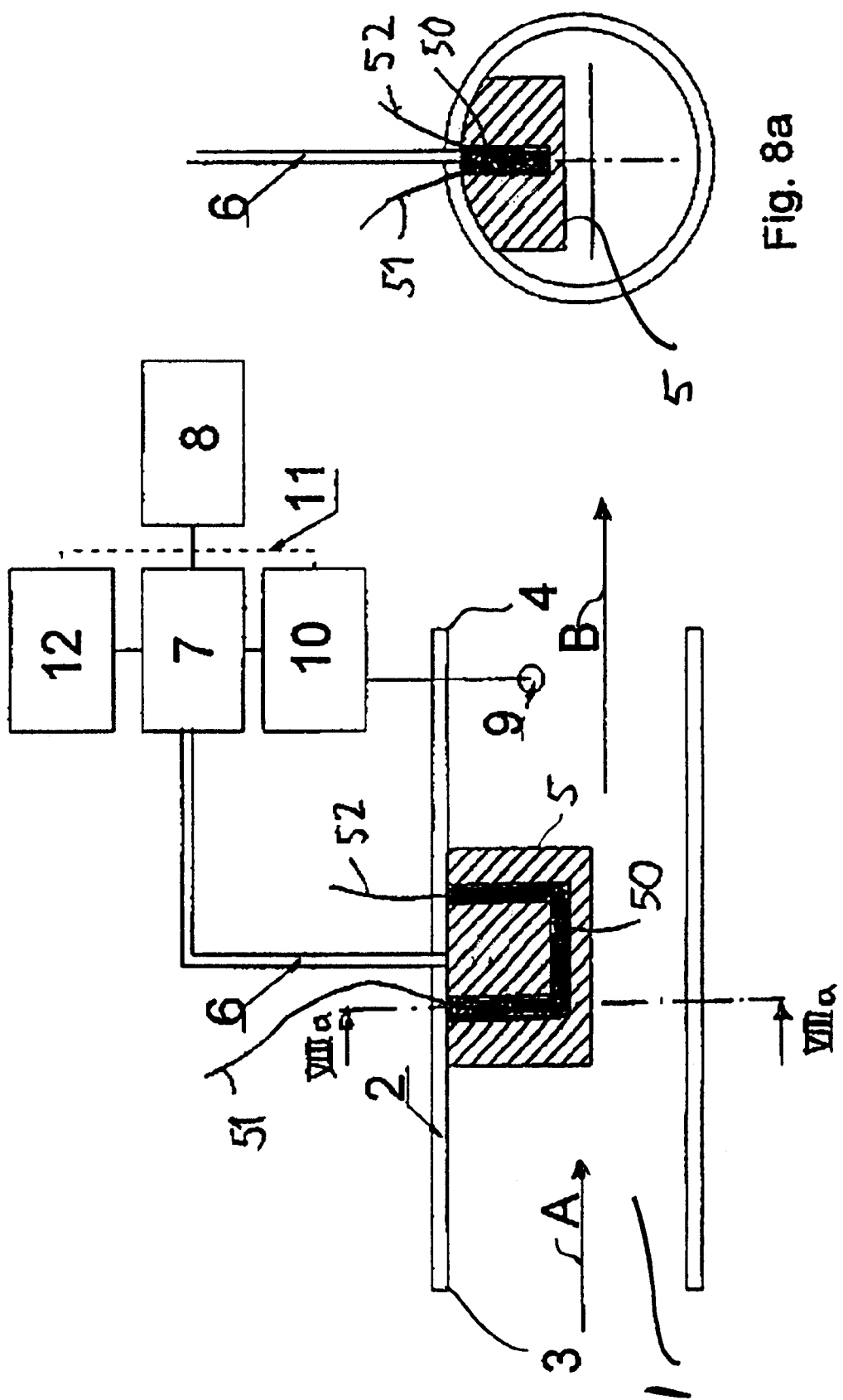

GAS SUPPLY APPARATUS AND METHOD FOR THE SUPPLY OF TREATMENT GAS TO A PERSON OR TO AN ANIMAL

CROSS REFERENCE TO RELATED APPLICATIONS

This application is a continuation of PCT/SE 98/00633, filed Apr. 6, 1998.

The present invention relates to an apparatus and method for supplying treatment gas, e.g., an anaesthetic, to a human being or to an animal.

FIELD OF INVENTION

Although the invention can be applied in a number of different applications in respect of supplying treatment gas to human beings and to animals, it finds particularly beneficial use in the anaesthesia of patients, in which case it is intended that the apparatus is connected to the system of hoses and devices by means of which breathing gas is supplied to a patient and to deliver the anaesthetic in a gasified state to the patient concerned.

DISCUSSION OF THE BACKGROUND

Anaesthetic vaporisers are well known to the art, and a large number of different methods have been described. With regard to known and used vaporisers, reference is made to Anaesthetic Equipment, C. S. Ward, published by Bailliere Tindall, 2nd edition, 1987, pp. 78–103 and to Anaesthesia Vaporisers by J. B. Eisenkraft in Anaesthesia Equipment, Principles and Applications, by Jan Ekrenwerth, James B. Eisenkraft, published by Mosby, 1993, pp. 57–58.

The earlier described vaporisers are based on the principle of storing liquid anaesthetic in a container into which there is introduced a breathing gas which passes over the liquid surface or bubbles through the liquid anaesthetic.

During this passage of the breathing gas, part of the anaesthetic is vaporised and entrained by the breathing gas to the patient. This method, however, is encumbered with a large number of problems.

1. As the anaesthetic is vaporised, energy is taken from the liquefied gas, which is therewith cooled. This cooling can result in a change in the vapour pressure above the surface of the liquid and therewith also change the amount of anaesthetic that is entrained by the breathing gas.

This problem has been dealt with by delivering additional heat in the case of some designs, or by varying the amount of breathing gas that passes over the liquid surface and then combining different gas flows so as to enable a constant anaesthetic content to be obtained in the breathing gas.

2. Vaporisation of the anaesthetic is dependent on the rate of flow of the breathing gas. Attempts to compensate for this dependency have been made by using different intricate flow-dependent valves and gas mixing systems in the vaporiser. The flow dependency can become problematic, particularly in the case of low fresh-gas flows that are used in so-called low flow systems.

3. Different anaesthetics have different vaporisation characteristics and need to be used in different concentrations for optimum anaesthesia. Attempts to compensate for this have been made by designing vaporisers that are each adapted for use with solely one anaesthetic. One drawback with this resides in the risk of filling a vaporiser with the wrong anaesthetic, i.e. with an anaesthetic for which it is not intended. This would have a catastrophic effect. The need for several different vaporisers to be mounted together on a single anaesthetic apparatus also involves the risk of all vaporisers being in operation simultaneously, with the accompanying risk of administering an anaesthetic overdose.

4. Anaesthetics have different vaporisation characteristics in different gas mixtures. This can result in administering to a patient a different amount of anaesthetic than that for which the vaporiser is set, due to the composition of the gas mixture.

5. A number of systems are based on the immersion of a wick in the anaesthetic. The anaesthetic is drawn up by the wick and vaporised on its surface. The drawback with this system, however, is that the rate at which the anaesthetic is drawn up the wick will depend on the height and temperature of the liquid surface, therewith necessitating the inclusion of a compensatory system in the vaporiser.

DE-A 4 105 163 teaches a anaesthetic vaporising system in which a porous body throughpassed by anaesthetic gases is saturated with anaesthetic.

The drawback with this system is that the amount of anaesthetic that shall be used is restricted by the absorbency of said body, and that evaporation of the anaesthetic in the passing gas will vary with time, due to lowering of the temperature of said body (due to evaporation of the gas). This means that a separate temperature control circuit must be provided in order for the system to function satisfactorily. There is no pump or active means for supplying liquefied gaseous anaesthetic to the absorption-desorption material.

U.S. Pat. No. 4,015,599 describes that the absorbent keeps anaesthetic in a two-dimensional state (it is not disclosed what is actually meant by this). The anaesthetic is kept in a liquid state by means of a wick. This system also utilises a pre-charged absorbent bed through which gases pass. The drawback with this system is that it also requires the use of a temperature control means and that different evaporation-absorption rates are obtained with different anaesthetic gases.

U.S. Pat. No. 3,540,445 describes a vaporiser in which fibrous wicks have been replaced with porous synthetic plastics that absorb the anaesthetic from a container through the medium of capillary forces. Although the container can admittedly be topped-up, the amount of anaesthetic taken up by the passing gas is primarily determined by the evaporation from the porous plastic rods and the capillary forces within these rods (when the level in a vessel filled with anaesthetic is kept constant), and consequently the apparatus becomes temperature-dependent and also dependent on the anaesthetic to be vaporised.

GB 2 255 912 describes a system that uses porous rods through which the gas passes on the one hand and which are passed by the gas on the other hand. These rods are supplied with gaseous anaesthetic, by submerging the rods in the anaesthetic. The level of anaesthetic in relation to the rods is regulated by a level regulator. It is necessary to regulate the rods and the temperature of the anaesthetic and the gas in order to obtain a stable concentration of anaesthetic in the gas.

GB 2 279 015 describes an apparatus in which the liquid to be vaporised is exposed to the gas, partly through porosities and partly through the free liquid surface, thereby also requiring the provision of temperature control means. The apparatus has no liquid quantity control facility.

SUMMARY OF THE INVENTION

The object of the present invention is to eliminate several of the drawbacks of the aforedescribed systems and to provide a method and apparatus that will provide uniform vaporisation of a large number of different anaesthetics in respect of a large number of different gas mixtures and flows.

The present invention relates to a gas supply apparatus and method for supplying a treatment gas, e.g., an anaesthetic, to a patient or animal using a porous liquid-emitting device connected to a liquid supply means which communicates with an external liquid source. The liquid to be vaporised is exposed exclusively to bypassing gas by way of the porosities in the liquid-emitting device.

The invention is thus based on delivering the liquid to be vaporised actively to the liquid emitting device, and is not therefore encumbered by the drawbacks associated with the type of system in which the vaporiser is charged with an initial quantity of liquid which is consumed during the process and the vaporisation process thereby influenced, i.e. such systems as those exemplified by the first three patent publications mentioned above.

The invention is based on the same liquid delay principle as that described in the aforementioned publication GB 2 255 912, according to which liquid is delivered constantly to the liquid emitting device from an external liquid source. However, those problems that accompany the construction of this apparatus with the inclusion of porous rods that are partially immersed in a liquid and with the free liquid surface in contact with the bypassing gas, and where the vaporisation process in the rods is sensitive to variations in liquid level have been avoided by means of the special features of the present invention. Thus, the liquid in the liquid emitting device is exposed solely through its porosities, so as to eliminate the effect of the level of a free liquid surface. Because the liquid is exposed solely via said porosities, the delivery of vaporised medium is determined solely by the delivery rate of the pump. Furthermore, there is provided a large and constant exposure surface area, so that the rate of evaporation will be at least equal to the liquid-emitting rate and can also be controlled, regulated, in a sure and purposeful manner.

The facility of enabling the liquid to be heated with the aid of the heating device enables the temperature of the liquid to be adapted in relation to the nature of liquid to be vaporised, so as to obtain optimum conditions with regard to the vaporisation process.

According to one preferred embodiment of the invention, the heating device is placed within the liquid-emitting device, therewith providing effective heating.

According to a second preferred embodiment, the heating device is placed outside but adjacent to the liquid-emitting device, therewith enabling the components to be arranged simply.

One quick and simple method of heating the liquid is to use a heating device in the form of an electric resistance, this embodiment comprising a further preferred embodiment of the invention.

According to another preferred embodiment, the liquid-emitting devices can be controlled so as to adapt readily to variations in requirements, for instance in response to different types of liquid to be vaporised.

In yet another preferred embodiment of the invention, the liquid is delivered by means of a pump, preferably a motor-driven pump, so as to provide safe and uniform supply of liquid and to enable the liquid supply to be readily regulated.

According to another preferred embodiment of the invention, the concentration of vaporised liquid in the outgoing air is preferably sensed by an optical sensor which appropriately controls the regulation of the amount of liquid supplied.

The aforedescribed embodiments and other preferred embodiments of the invention are set forth in the dependent claims.

The invention will now be described in more detail with reference to preferred embodiments of the invention and also with reference to the accompanying drawings.

BRIEF DESCRIPTION OF DRAWINGS

FIGS. 6–8, 6a–8a illustrate alternative embodiments in a manner corresponding to FIG. 1.

DETAILED DESCRIPTION OF PREFERRED EMBODIMENTS

Figure 1:
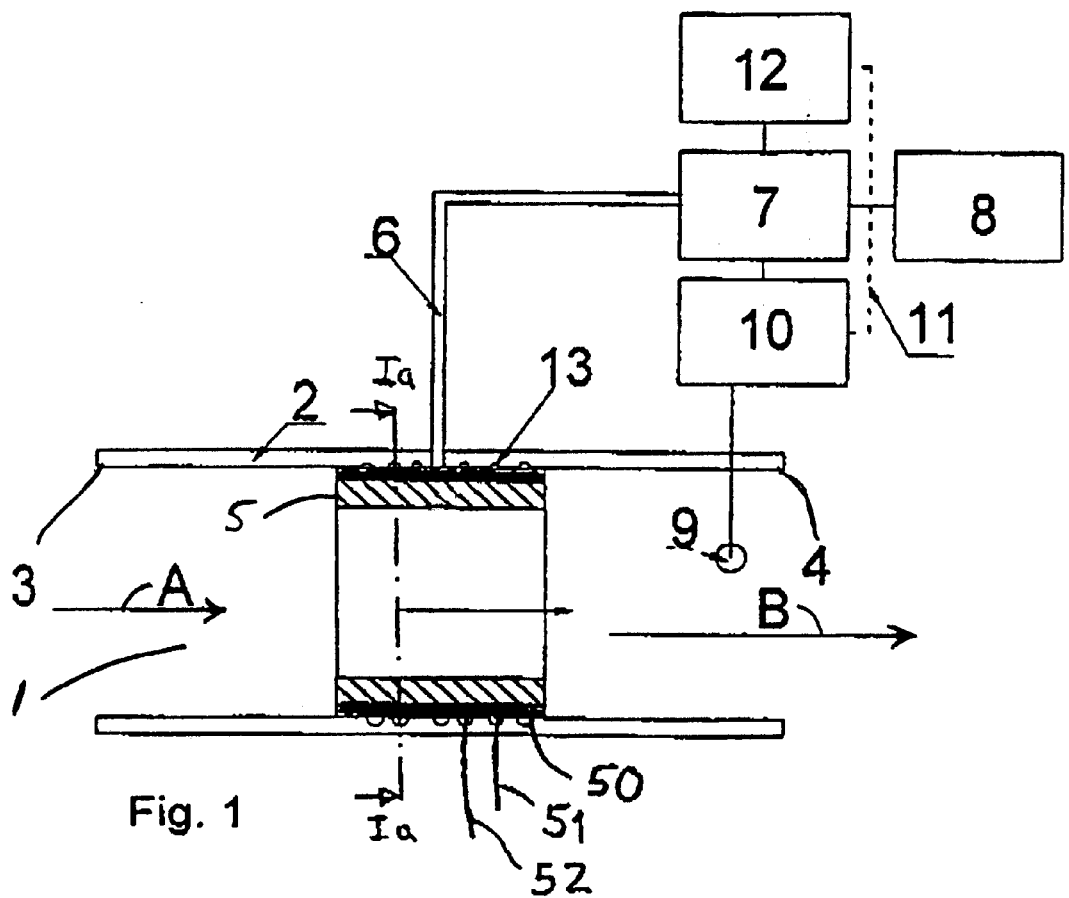
FIG. 1 is a principle diagram illustrating an apparatus according to a preferred embodiment of the invention.

The apparatus illustrated in FIG. 1 includes a vaporising chamber 1 formed by a container 2. Although the container is shown to have a tubular shape it will be understood that it may have any other desired shape. The vaporisation chamber 1 has an inlet opening 3 which is connected to a gas delivery inlet line, (not shown) as symbolised with the arrow A, and an outlet opening 4 which is connected to a gas discharge outlet line (not shown), symbolised with the arrow B. The outlet line is intended for connection with the respiratory organs of a patient for the delivery of, in this case, anaesthetic gas. Arranged in the vaporisation chamber 1 is a liquid-emitting device 5 in the form of a porous body. The porous body has a cylindrical shape and is conveniently made of plastic material. A delivery line 6 for the delivery of anaesthetic in liquid form is connected to the liquid-emitting device 5.

As the gas flows from the inlet 3 and through the chamber 1 to the outlet 4, it passes the liquid-emitting device 5 and comes into contact with the liquid present in the porosities of said device. As the liquid is exposed to the bypassing gas, the liquid will be vaporised by evaporation. Fresh liquid is constantly delivered from the delivery line 6 through the passageways formed by the inner porosities of the porous body out to the surface-located porosities, such that the process will be continuous in principle. The outflowing gas B will therewith contain a certain amount of vaporised anaesthetic.

The liquid delivered from the delivery line 6 is led directly to the porosities in the liquid-emitting device 5. The delivery is thus active and does not take place via a reservoir arranged in the proximity of the liquid-emitting device and from which liquid is drawn into the porosities via capillary action. This avoids the control problems and uniform flow problems that result from such capillary supply. Because the liquid is delivered directly to the porosities, the liquid will also be exposed to the gas exclusively via said porosities and not via a free liquid surface. In the embodiment shown, liquid-emitting device 5 lies against the inner surface of the wall of the vaporisation chamber. The inner surface of the wall includes grooves 13 which communicate with the liquid delivery line 6.

In the illustrated example, liquid anaesthetic is delivered from an external anaesthetic container 8 to the liquid-emitting device 5 through the medium of a pump 7.

Alternatively, the external container 8 can be positioned at a height sufficient to deliver the liquid gravitationally. In the case of this alternative embodiment, the pump 7 is replaced with a control valve.

A sensor 9 is mounted in the path of gas flow, downstream of the liquid-emitting device 5. The sensor may be an optical sensor that senses the optical absorption of the gas at different light wavelengths. Alternatively, the sensor may have a form of an opening connected to a hose for withdrawing a gas sample. The sensor 9 is coupled to a signal unit 10 which, via a signal line 11, sends signals to a control unit 12 that controls the pump 7.

When an optical sensor is used, the signal unit 10 is comprised of a signal converter which, depending on the sensor reading, forwards a relevant signal to the control unit 12. When the sensor 9 has the form of a gas sampler, the signal unit 10 includes analysis instruments which analyse the gas content and send signals to the control unit 12 on the basis of this analysis.

The control unit 12 may be an electric, electronic or electromechanical unit, although a microprocessor controlled unit is preferred. The control unit influences the pump flow solely by varying the operational resistance of the motor or by directly varying the operating state of the pump. The control unit 12 and the pump 7 may conveniently be incorporated as one single unit. The pump may be an injector pump.

The aforedescribed control apparatus is effective in controlling the amount of liquid anaesthetic delivered to the liquid-emitting device 5 per unit of time on the basis of the concentration of anaesthetic in the departing gas B.

An electrical resistance 50 with connection lines 51, 52 is arranged between the liquid-emitting device 5 and the wall of container 2. The resistance 50 functions to heat the liquid present in the liquid-emitting device.

FIGS. 2 to 5 illustrate different ways of connecting the inventive vaporising apparatus in a system for delivering anaesthetic gas to a patient.

Figure 2:
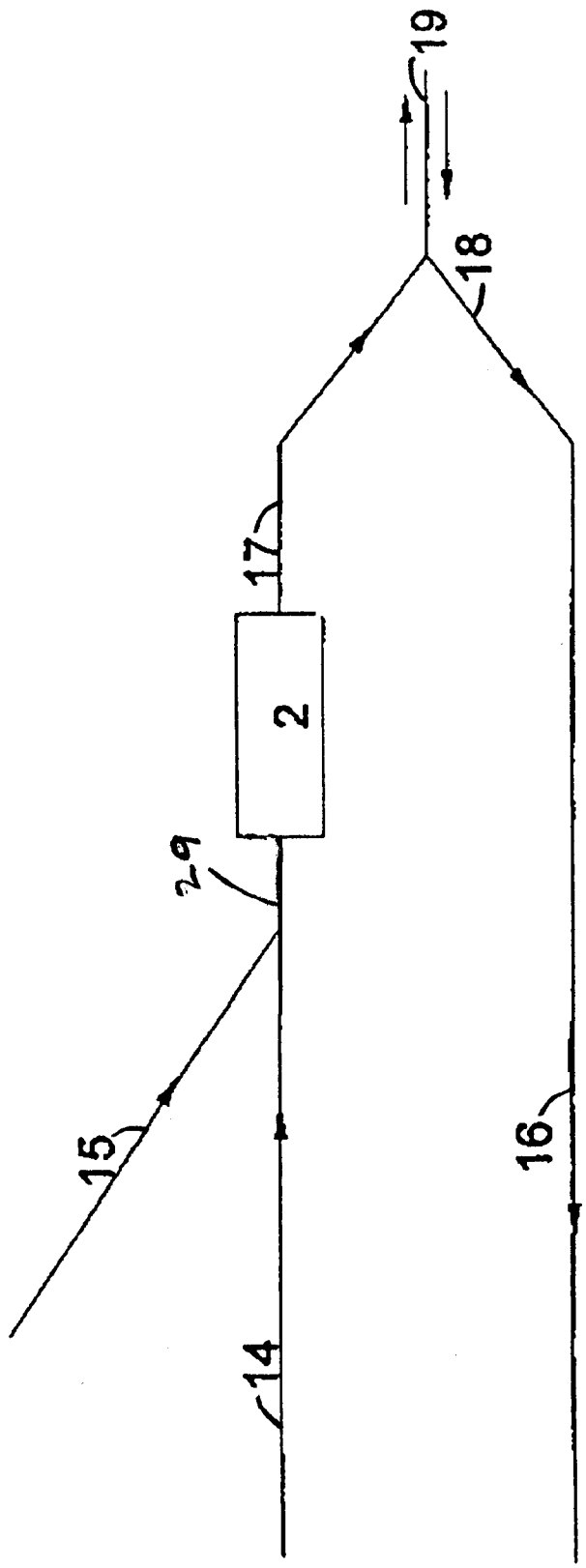
FIGS. 2–5 illustrate schematically various ways of connecting the inventive apparatus when using said apparatus in an anaesthesia system.

In the FIG. 2 embodiment, the gas flowing into the container 2 through the gas delivery line 29 is comprised of a mixture of fresh gas entering from a line 15 and recycled gas entering from a line 14. The anaesthetic-containing gas is led on the outlet side through the line 17 to a line 19 leading to the patient, via a Y-coupling 18. The other branch of the Y-coupling 18 is comprised of the line 16 for exhalation gas.

Figure 3:
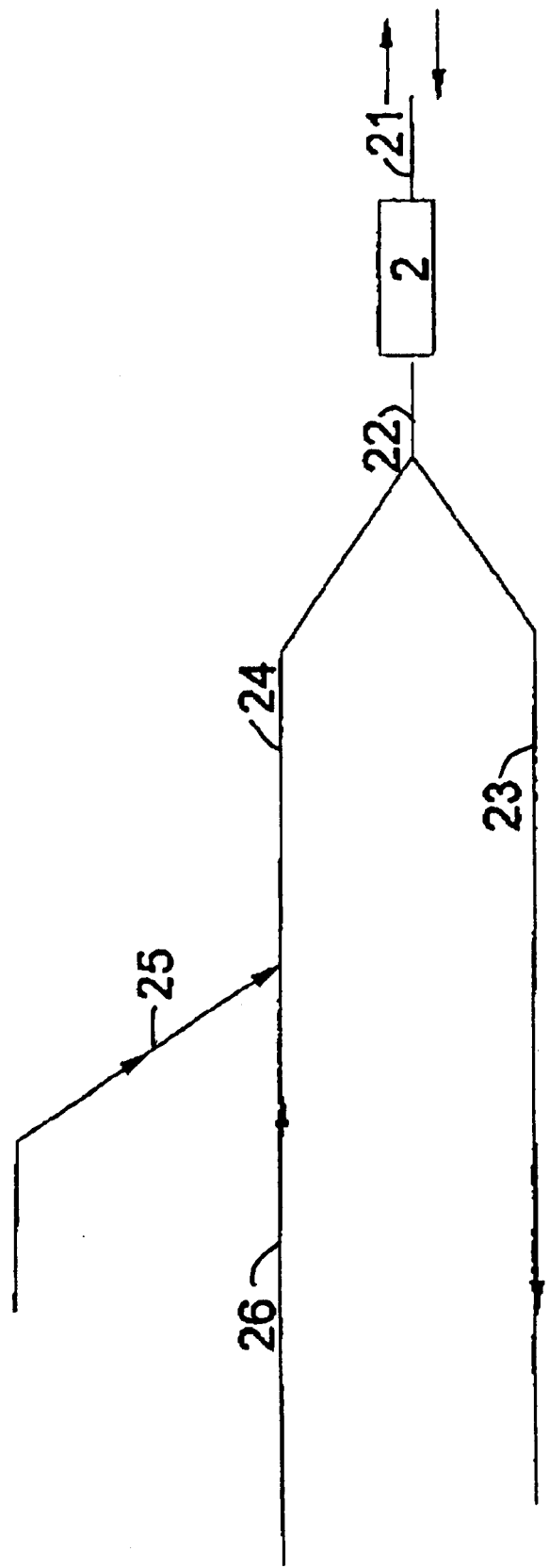

The coupling shown in FIG. 3 is modified inasmuch that the container 2 is connected between the Y-coupling 22 and the patient supply line 21. Reference numeral 24 identifies the inhalation hose, 26 identifies the fresh gas hose, reference 26 identifies the hose for re-circulated gas, and 23 identifies the exhalation hose.

Figure 4:
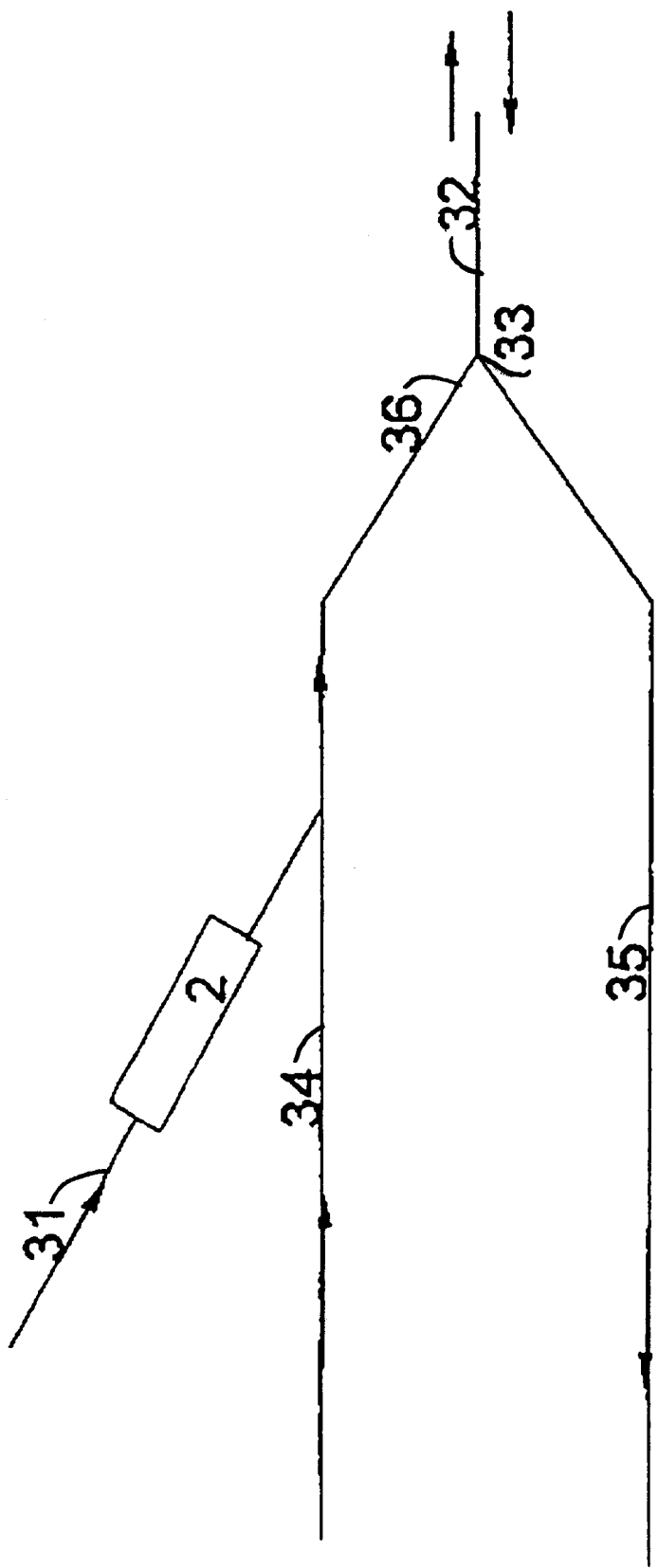

In the FIG. 4 embodiment, the container 2 is arranged in the fresh gas hose 31. In FIG. 3, the reference 32 identifies the patient supply hose, 33 identifies the Y-coupling, 34 identifies the hose for re-circulated gas, 35 identifies the exhalation hose, and 36 identifies the inhalation hose.

Figure 5:
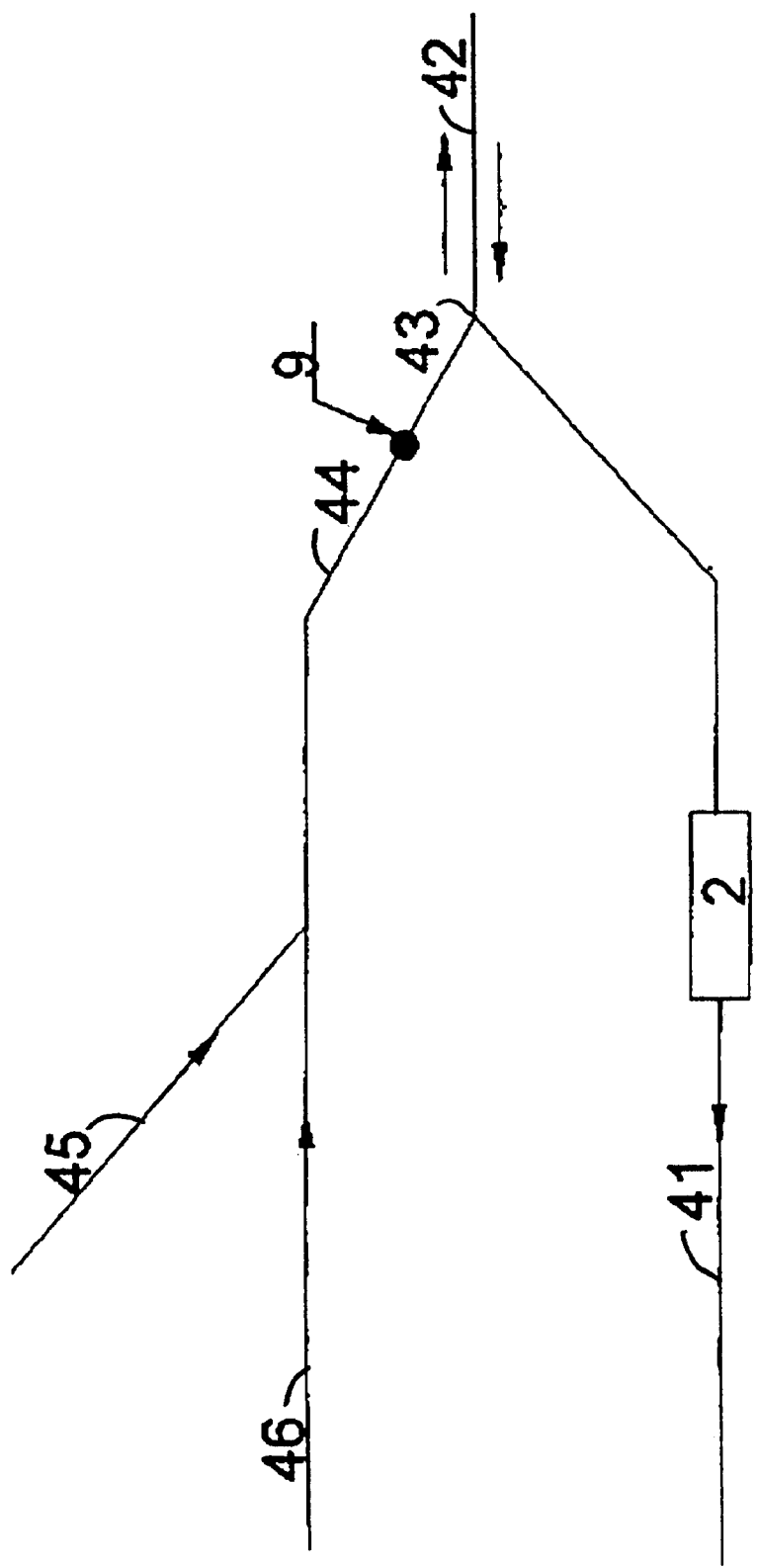
Figure 6A:
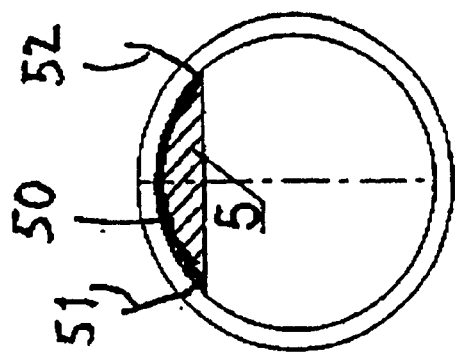
Figure 6:
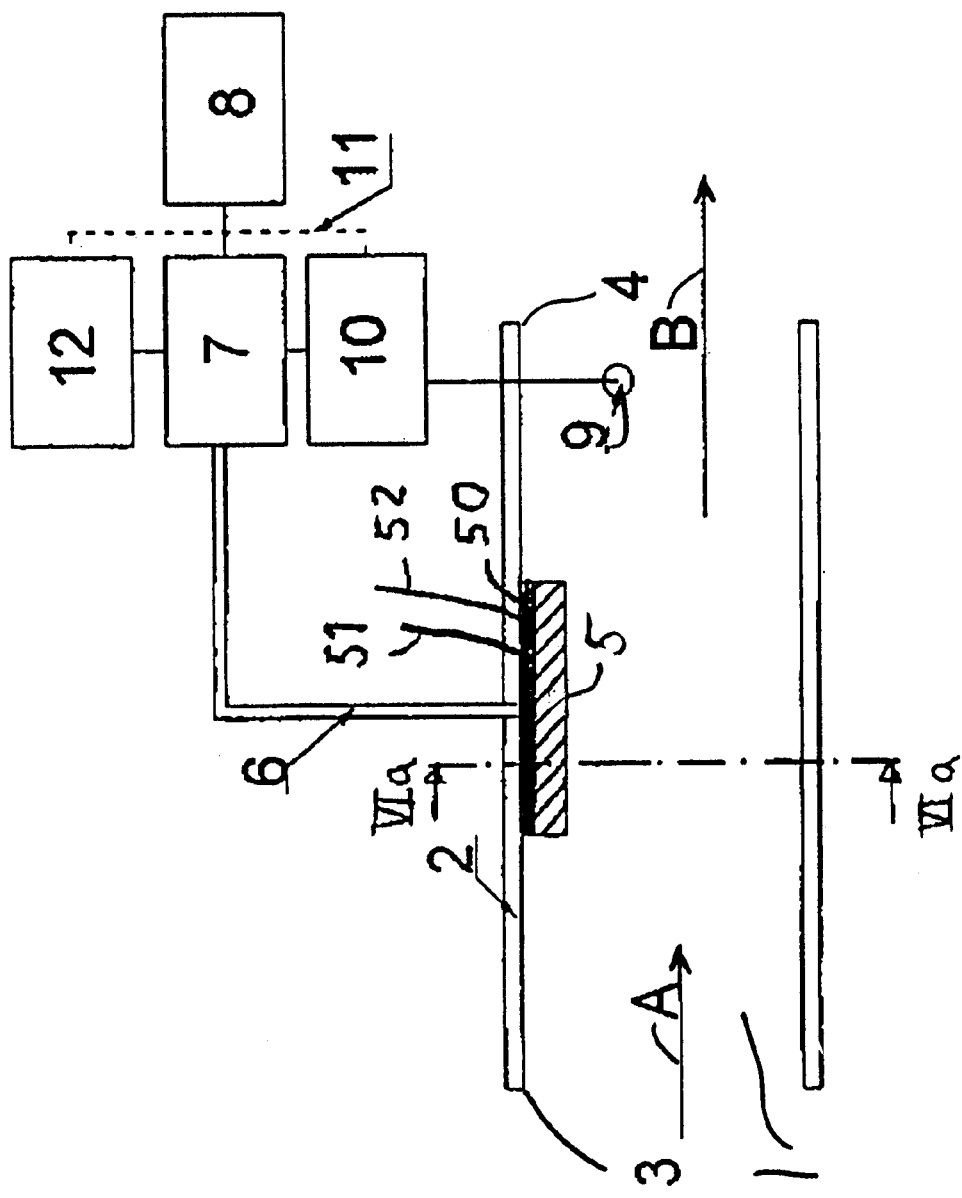

In the alternative shown in FIG. 5, the container 2 is placed in the exhalation hose 41. Reference 42 identifies the patient supply hose, 44 identifies the inhalation hose, 45 identifies the fresh air hose, and 46 identifies the hose for re-circulated gas. In the case of this coupling, the sensor 9 is placed separately from other components in the vaporising apparatus, although it is, of course, in signal communication therewith.

In the case of the FIG. 5 embodiment, the gas is enriched with anaesthetic in the exhalation hose 41, so that the recirculation hose 46 will convey gaseous anaesthetic. That part of the exhalation hose 41 located downstream of the container 2, the re-circulation hose 46, and the inhalation hose 44 all form parts of the container outlet line.

Figure 1A:
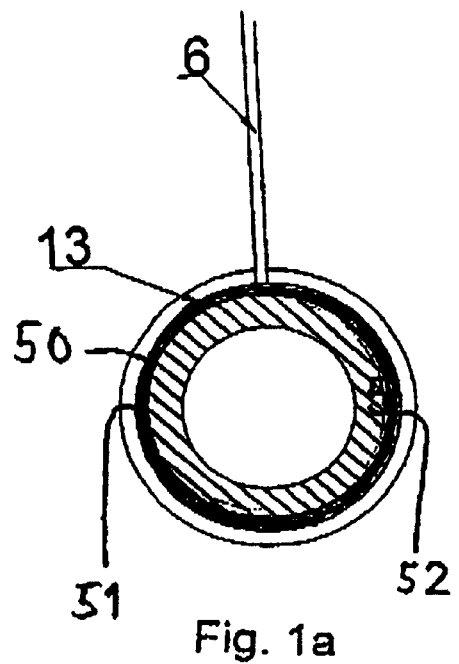
FIG. 1a is a sectional view taken on the line I—I in FIG. 1.

The apparatus illustrated in FIGS. 6–8, 6a–8a exemplify modified embodiments of the liquid-emitting device 5, although these apparatus are, in general, identical with the embodiment according to FIGS. 1, 1a. In the embodiment according to FIGS. 6, 6a, the body 5 has a segmental form, in FIGS. 7, 7a a form which is elongated transversely to the flow direction, and in FIGS. 8, 8a a block-like form which is rounded to conform to the inner surface of the container 2. As illustrated, the heating device 50 may be placed within the liquid-emitting device 5 in both of these latter embodiments.

What is claimed is:

1. Gas supply apparatus for the supply of treatment gas, e.g., an anaesthetic, to a human being or to an animal, wherein the apparatus has a vaporiser which includes a vaporising chamber that has a gas inlet means and a gas outlet means and in which a porous liquid-emitting device is arranged to expose a liquid to said vaporising chamber for vaporisation of liquid, and wherein the liquid-emitting device is connected to a liquid supply means which communicates with an external liquid source, and wherein the gas outlet means is adapted for connection to an inhalation means, characterized in that said liquid-emitting device lies against the inner surface of a wall of said vaporising chamber and wherein said liquid supply means delivers said liquid directly to said liquid-emitting device whereby the liquid is exposed exclusively via the porosities in the liquid-emitting device; and in that the apparatus includes liquid-heating means.

2. Apparatus according to claim 1, wherein the heating means is adapted to heat the liquid present in the liquid-emitting device.

3. Apparatus according to claim 2, wherein the heating means is arranged within the liquid-emitting device.

4. Apparatus according to claim 2, wherein the heating means is arranged externally of but adjacent to said liquid-emitting device.

5. Apparatus according to any one of claim 1, wherein the heating means is an electrical resistance.

6. Apparatus according to any one of claim 1, wherein the liquid supply means is provided with liquid-quantity control means.

7. Apparatus according to any one of claim 1, wherein said liquid supply means includes a pump.

8. Apparatus according to claim 7, wherein the pump is motor-driven.

9. Apparatus according to claim 7, wherein the pump is a controllable pump and therewith constitutes a component in said liquid-quantity control means.

10. Apparatus according to claim 8, wherein the apparatus includes sensor means for sensing the vaporised liquid content, said sensor means being located downstream of said liquid-emitting device.

11. Apparatus according to claim 10, wherein said sensor means includes an optical sensor.

12. Apparatus according to claim 10, wherein said liquid-quantity control means is adapted to regulate the supply of liquid in response to said sensor means.

13. Apparatus in accordance with claim 8, wherein said liquid-quantity control means is adapted to deliver per unit of time a quantity of liquid that is at most equal to the quantity of liquid that is vaporised in said liquid-emitting device per unit of time.

14. Apparatus according to claim 1, wherein said liquid-emitting device is comprised of a plastic material.

15. Apparatus according to claim 1, wherein the wall includes on the surface thereof that lies against the liquid-emitting device grooves which communicate with said liquid supply means.

16. Apparatus according to claim 1, wherein the liquid-emitting device has the form of a hollow cylinder.

17. A method of supply treatment gas to the respiratory organs of a human being or an animal, wherein liquid is delivered from an external liquid source to a porous liquid-emitting device in which the liquid is exposed to a flowing gas so as to vaporise upon contact with said gas, whereafter the vapour is delivered to said respiratory organs, said method comprising delivering said liquid directly to said liquid-emitting device and exclusively exposing said liquid to said gas via the porosities of said liquid-emitting device.

18. A method according to claim 17, wherein the liquid is heated when present in the liquid-emitting device; and in that heating is effected electrically.

19. A method according to claim 18, wherein the supply of liquid is regulated.

20. A method according to claim 17, wherein the liquid is delivered with the aid of a motor-driven pump.

21. A method according to claim 17, wherein the gasified liquid content of the gas is sensed after its contact with the liquid with the aid of an optical sensor; and in that the amount of liquid delivered per unit of time is controlled on the basis of this sensed content.

* * * * *